(12) United States Patent
Schulz et al.

(10) Patent No.: US 8,948,483 B2
(45) Date of Patent: Feb. 3, 2015

(54) AUTOMATED CONTRAST ENHANCEMENT FOR CONTOURING

(75) Inventors: Heinrich Schulz, Hamburg (DE); Daniel Bystrov, Hamburg (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/260,936

(22) PCT Filed: Feb. 18, 2010

(86) PCT No.: PCT/IB2010/050734
§ 371 (c)(1),
(2), (4) Date: Sep. 29, 2011

(87) PCT Pub. No.: WO2010/113047
PCT Pub. Date: Oct. 7, 2010

(65) Prior Publication Data
US 2012/0032953 A1     Feb. 9, 2012

Related U.S. Application Data

(60) Provisional application No. 61/165,025, filed on Mar. 31, 2009.

(51) Int. Cl.
*G06K 9/00* (2006.01)
*G06T 7/00* (2006.01)
*G06T 5/00* (2006.01)

(52) U.S. Cl.
CPC .............. *G06T 5/008* (2013.01); *G06T 7/0083* (2013.01); *G06T 2207/30004* (2013.01); *G06T 2207/10072* (2013.01); *G06T 2207/20104* (2013.01); *G06T 2207/20012* (2013.01)
USPC ......................................................... 382/131

(58) Field of Classification Search
None
See application file for complete search history.

(56) References Cited

U.S. PATENT DOCUMENTS

| 5,042,077 | A | 8/1991 | Burke |
| 6,353,674 | B1 * | 3/2002 | Dewaele ....................... 382/132 |
| 7,149,333 | B2 * | 12/2006 | Pieper et al. .................. 382/128 |
| 7,158,692 | B2 * | 1/2007 | Chalana et al. ............... 382/294 |
| 7,218,763 | B2 * | 5/2007 | Belykh et al. ................. 382/128 |
| 7,236,618 | B1 * | 6/2007 | Chui et al. .................... 382/128 |
| 7,565,000 | B2 * | 7/2009 | Capolunghi et al. .......... 382/128 |
| 8,285,010 | B2 * | 10/2012 | Rowe ............................ 382/124 |
| 2001/0033283 | A1 | 10/2001 | Liang et al. |
| 2006/0098010 | A1 * | 5/2006 | Dwyer et al. ................. 345/424 |
| 2007/0116335 | A1 * | 5/2007 | Capolunghi et al. .......... 382/128 |

(Continued)

FOREIGN PATENT DOCUMENTS

JP       03617698 B       2/2005

OTHER PUBLICATIONS

By R Sakellaropoulos et al.; Entitled: "An Image Visualization Tool in Mammorgraphy"; Published in: Informatics for Health and Social Care; vol. 24, Issue 1 Jan. 1999, p. 1 of 1.

*Primary Examiner* — Nancy Bitar

(57) ABSTRACT

A system and method for automatic contrast enhancement for contouring. The system and method including displaying a volumetric image slice to be analyzed, receiving a delineation of a target anatomic structure in the volumetric image slice, identifying a region of interest based upon an area being delineated in the volumetric image slice, analyzing voxel intensity values in the region of interest and determining an appropriate window-level setting based on the voxel intensity values.

16 Claims, 3 Drawing Sheets

(56) References Cited

U.S. PATENT DOCUMENTS

| | | | |
|---|---|---|---|
| 2010/0130860 A1* | 5/2010 | Yamagata | 600/443 |
| 2011/0313285 A1* | 12/2011 | Fallavollita et al. | 600/426 |
| 2012/0269413 A1* | 10/2012 | Hautvast et al. | 382/128 |

* cited by examiner

AUTOMATED CONTRAST ENHANCEMENT FOR CONTOURING

BACKGROUND

Segmentation is the process of extracting anatomic configurations from images. Many applications in medicine require segmentation of standard anatomy in volumetric images acquired from CT, MRI and other imaging devices. Clinicians, or other professionals, often use segmentation for treatment planning. For example, segmentation may be used for radiation therapy planning such that radiation treatment may be delivered, at a desired dosage, to a target tissue. Currently, segmentation can be performed manually, in which the clinician examines individual image slices and manually draws two-dimensional contours of a relevant organ in each slice. The hand-drawn contours are then combined to produce a three-dimensional representation of the relevant organ. Alternatively, the clinician may use an automatic algorithm for segmentation.

Most structures, however, are still delineated manually slice-by-slice in volumetric medical datasets. Segmentation by hand is tedious and time-consuming, requiring significant expert knowledge to execute. For example, for some applications like radiotherapy in the head and neck region, the segmentation step is one of the main limitations for patient throughput in the clinical workflow. Generally, the clinician must select a slice of the image in which the structure is clearly visible and window-level settings may be manually adjusted to such that a particular region of the image is more clearly visible. Subsequently the contouring process is continued in adjacent slices. As the image contrast often changes from slice to slice, visualization settings such as the window-level setting must be adjusted accordingly for each slice. Manually adjusting the window-level settings for each subsequent image slice or for various regions of a single image slice is time-consuming and tedious.

SUMMARY OF THE INVENTION

A method for automatic contrast enhancement for contouring. The method including displaying a volumetric image slice to be analyzed, receiving a delineation of a target anatomic structure in the volumetric image slice, identifying a region of interest based upon an area being delineated in the volumetric image slice, analyzing voxel intensity values in the region of interest and determining an appropriate window-level setting based on the voxel intensity values.

A system having a display displaying a volumetric image slice to be analyzed, a user interface capable of accepting a user delineation of a target anatomic structure in the volumetric image slice and a processor identifying a region of interest based on the user delineation and analyzing a voxel intensity value of the region of interest to determine an appropriate window-level setting.

A computer-readable storage medium including a set of instructions executable by a processor. The set of instructions operable to display a volumetric image slice to be analyzed, receive a delineation of a target anatomic structure in the volumetric image slice, identify a region of interest based upon an area being delineated in the volumetric image slice, analyze voxel intensity values in the region of interest and determine an appropriate window-level setting based on the voxel intensity values.

DETAILED DESCRIPTION

Figure 1:
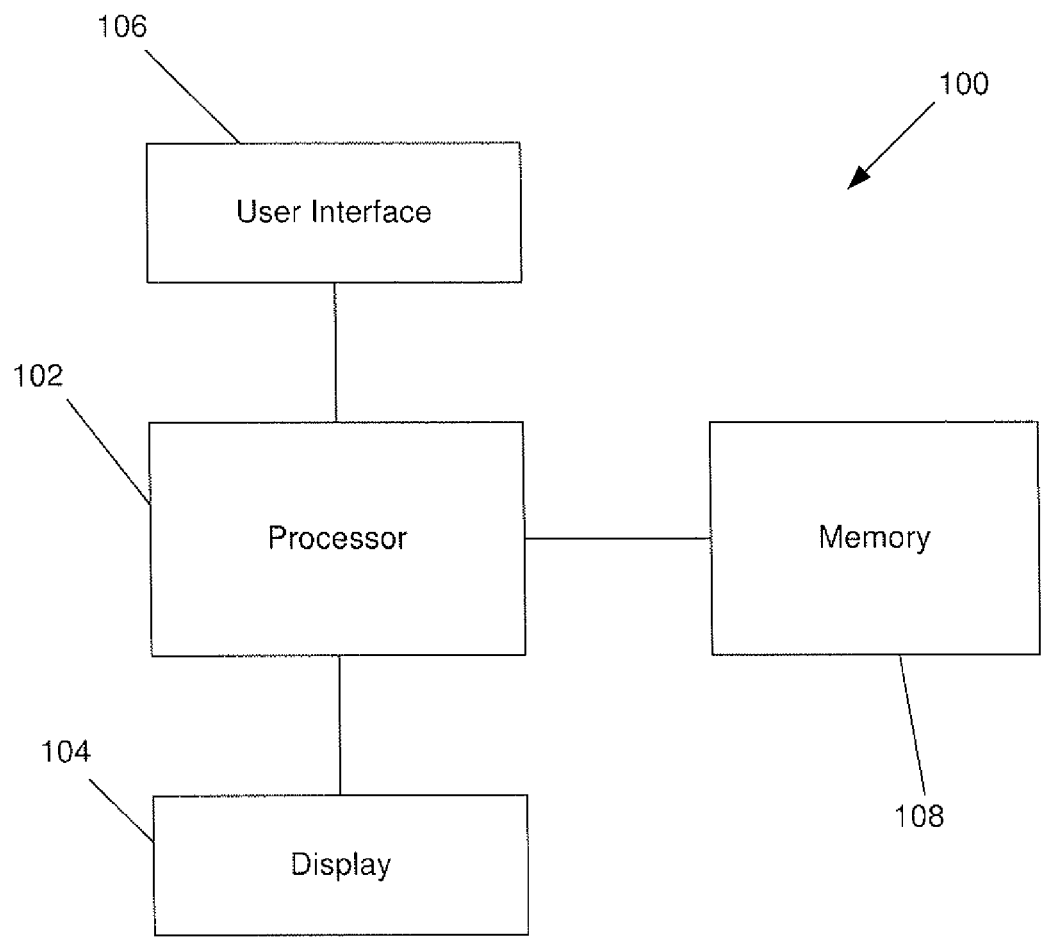
FIG. 1 shows a schematic diagram of a system according to an exemplary embodiment of the present invention.

The exemplary embodiments set forth herein may be further understood with reference to the following description and the appended drawings, wherein like elements are referred to with the same reference numerals. The exemplary embodiments relate to a system and method for segmentation of a standard anatomy in volumetric images acquired from CT, MRI, etc. In particular, exemplary embodiments set forth herein describe a method for automatically adjusting image visualization in volumetric images such that a target structure may be easily distinguished from neighboring structures.

FIG. 1 shows an exemplary embodiment of a system 100 for automatically adjusting window-level settings such that a target anatomic structure is optimally visible in an image slice being analyzed. The system 100 comprises a processor 102 for mapping window-level settings to voxel intensity values, a display 104 for displaying volumetric images and a user interface 106 for drawing a target anatomic structure being contoured from slices of the volumetric images. The system 100 further comprises a memory 108 for storing the images and/or the window level settings. The memory 108 may be any known computer readable storage medium. It will be understood by those of skill in the art that the system 100 may be a personal computer or any other processing arrangement.

Figure 2:
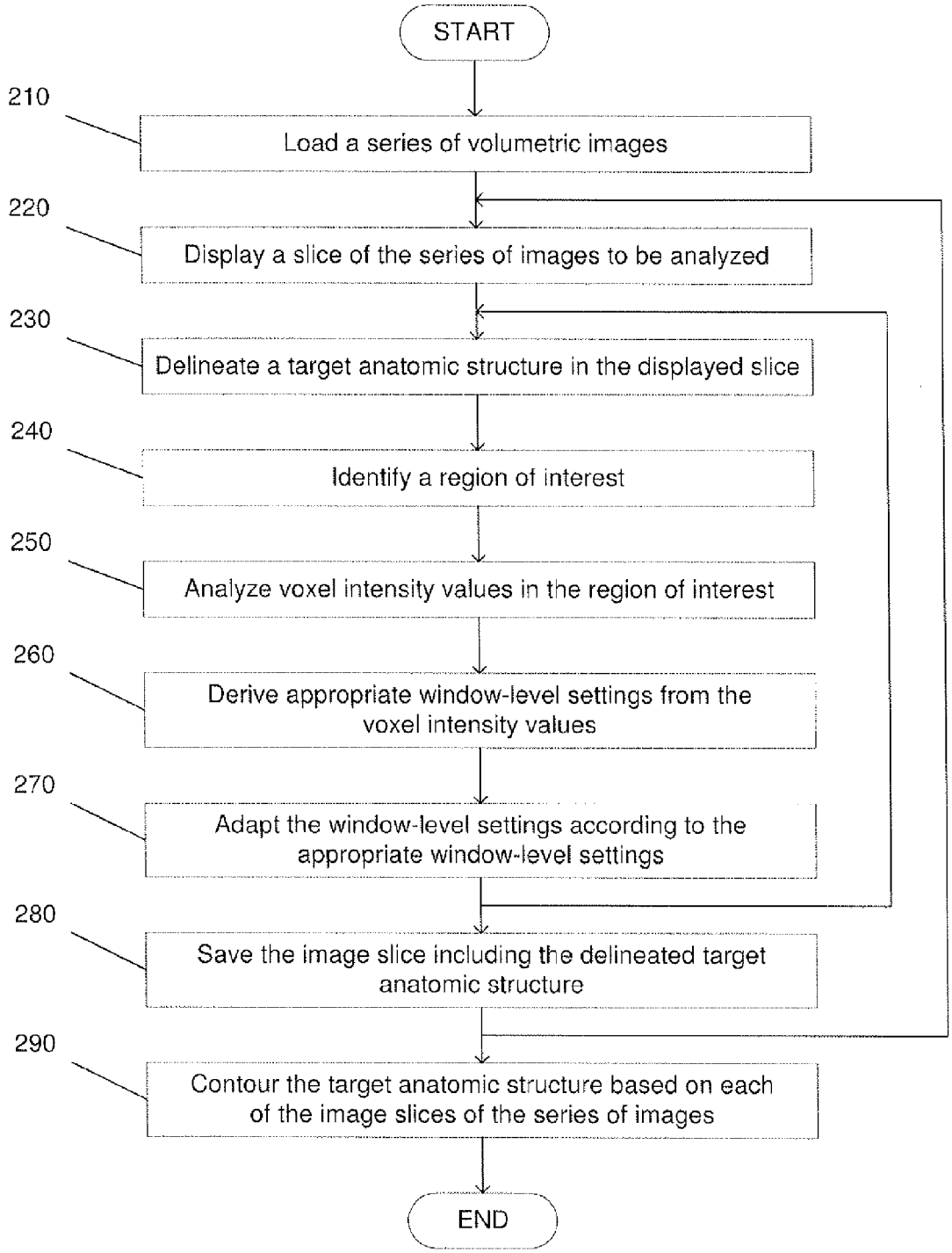
FIG. 2 shows a flow diagram of a method according to an exemplary method of the present invention.

FIG. 2 shows an exemplary method 200 which comprises loading a series of volumetric images into the exemplary system 100 shown in FIG. 1, in a step 210, such that the series of volumetric images may be analyzed by a user slice by slice. The series of images are for example stored in the memory 108 of the system 100 and are loaded such that the series of images are displayed on the display 104. It will be understood by those of skill in the art that the display 104 may display one or more slices of the series of images at a time. It will also be understood by those of skill in the art that while loading the series of images, the processor 102 may determine a number (N) of image slices that exists in the series of images being loaded. In a step 220, the user views and analyzes a slice of the series of images to identify the target anatomic structure. In a step 230, the user draws the anatomic structure onto the image slice, delineating the target anatomic structure. The user draws on the image via the user interface 106. The user interface 106 consists of a mouse for example, which is used to point to and click on the region of interest by outlining the target anatomic structure. The display 104 may alternatively include touch sensitivity such that the user may draw directly onto the image via the display 104 using a stylus or other detectable touch mechanism.

Figure 3A:
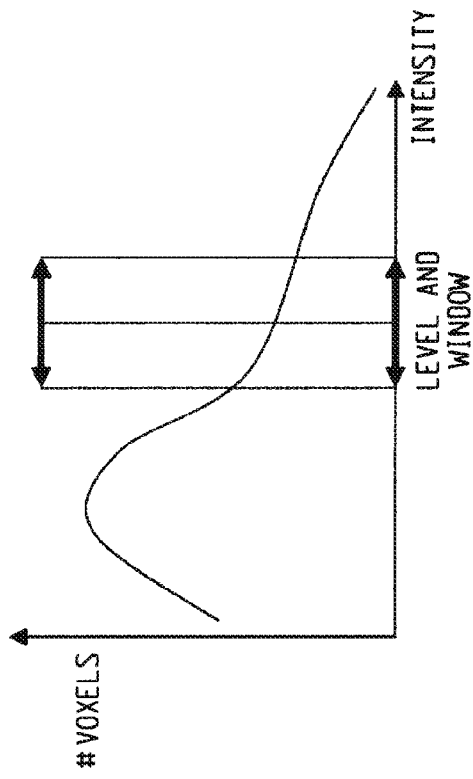
FIG. 3 shows the influence of a window-level setting on image visualization according to the method of FIG. 2.
Figure 3A:
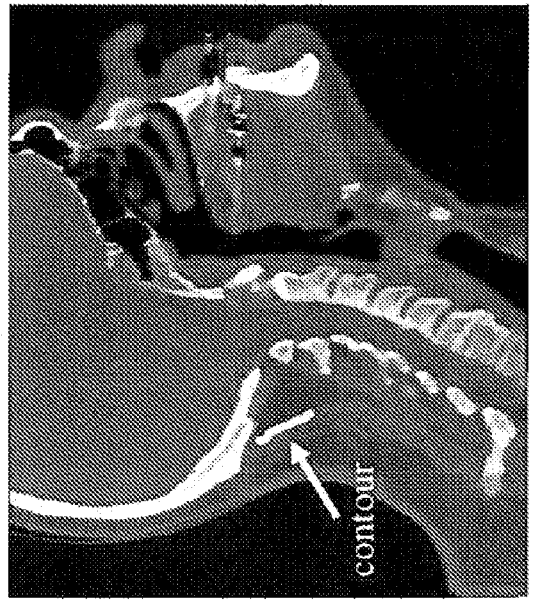

The processor 102 identifies a region of interest, in a step 240. The region of interest is identified as a portion of the image, which is determined by an area of the image in which the user is drawing. The processor 102 then analyzes voxel intensity values in the region of interest, in a step 250. The voxel intensity values are analyzed via an intensity histogram drawn by the processor 102. It is well known in the art that a voxel represents a volume element in a three dimensional space. The intensity histogram is a graph showing the number of voxels in an image, at each different intensity value found in that image. It will be understood by those of skill in the art that a wide range of intensity values may exist in a grayscale image, from the darkest of blacks to the lightest of whites. For example, as shown in FIG. 3A, an intensity histogram is shown for an image slice in which a neck portion is the region of interest and a cervical vertebrae is the target anatomic structure. A current window-level setting for the image slice is also shown.

Figure 3B:
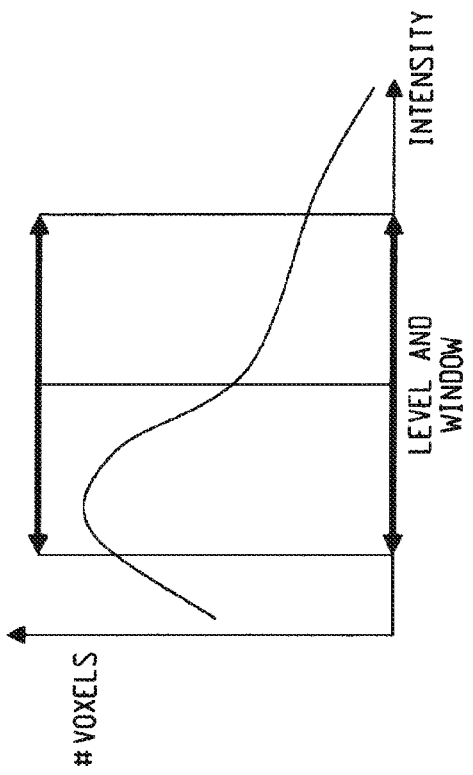
Figure 3B:
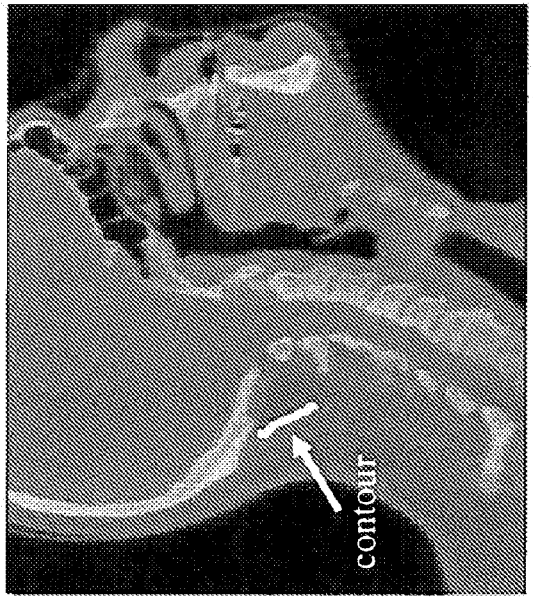

Based upon the voxel intensity values analyzed in step 250, an appropriate window-level setting for optimal visibility of the region of interest is derived in a step 260. The window-level settings are, for example, defined based on maximum and minimum image gray values in the region of interest. An interval between the maximum and minimum gray values may be mapped to an interval available for display in a linear fashion. For example, the minimum value may be mapped to pure black while the maximum value may be mapped to pure white to provide greater contrast for the image displayed on the display 104. Alternatively, a non-linear transfer function may be used to enhance display contrast along edges of the displayed image. As shown in FIG. 3B, appropriately adjusting window-level settings increases the display contrast of the image. In a step 270, the current window-level setting for the image slice is adjusted according to the appropriate window-level setting derived in step 260. As shown in FIG. 3B, the window-level setting is adjusted such that the target anatomic structure in the region of interest has increased visibility. Thus, the target anatomic structure is easier to delineate by the user, thereby increasing accuracy of the segmentation process. As the current window-level setting is adjusted, the user may continue to delineate the target anatomic structure, the method 200 returning to the step 230, such that the processor 102 continues to identify the region of interest and adjust the window-level settings accordingly in steps 240-270. Thus, it will be understood by those of skill in the art that the window-level setting continues to automatically adjust as the user delineates the target anatomic structure in the image slice.

It will also be understood by those of skill in the art that the window-level settings may be adjusted prior to any delineation of the target anatomic structure by the user. Where the target anatomic structure is not delineated, the method 200 moves directly from step 220 to step 240, identifying the region of interest as the entire displayed image slice. Voxel intensity values of the entire image slice are analyzed in the step 250, appropriate window-level settings derived in the step 260, and the window-level settings adapted accordingly, in the step 270. Once the window-level setting has been adjusted, the method 200 returns to the step 230 so that the user may begin delineation of the target anatomic structure.

Once the target anatomic structure has been completely delineated by the user in the image slice, the image slice, including markings showing the delineated target anatomic structure, may be stored in the memory 108 in a step 280, such that the series of images may be later processed for contouring after each of the image slices in the series of images has been delineated by the user. The appropriate window-level setting corresponding to the image slice may also be stored in the memory 108.

The window-level may automatically adjust from slice to slice so long as there is an additional slice in the series of images to be analyzed and drawn. Thus, where there is an additional slice, the method 200 returns to the step 220. In the step 220, the processor 102 displays on the display 104 a slice of the image that is to be analyzed. Thus, it will be understood by those of skill in the art that for each cycle of the method 200, the processor 102 displays slices of the series of images that have not yet been analyzed such that each subsequent cycle displays a new slice of the series of images. After displaying another slice, the method 200 returns to step 220. It will be understood by those of skill in the art that the method 200 will continue to return to step 220 from the step 280, N−1 times. On the Nth time, however, the method 200 continues to a step 290, where the processor 102 processes the delineated target anatomic structure in each of the image slices of the series of images to contour the three dimensional target anatomic structure.

It will be understood by those of skill in the art that the user may adjust parameter settings according to user preferences, via the user interface 106. For example, the user may determine whether to delineate the target anatomic structure in each of the image slices in the series of images such that only a subset of image slices in the series of images may be delineated. It will also be understood by those of skill in the art that the user may also make manual adjustments to window-level settings, when necessary. Manual adjustments to window-level settings may be incorporated into the automatic adaptation of the window-level setting, as described above.

It is noted that the exemplary embodiments or portions of the exemplary embodiments may be implemented as a set of instructions stored on a computer readable storage medium, the set of instructions being executable by a processor.

It will be apparent to those skilled in the art that various modifications may be made to the disclosed exemplary embodiments and methods and alternatives without departing from the spirit or the scope of the disclosure. Thus, it is intended that the present disclosure cover modifications and variations provided they come within the scope of the appended claims and their equivalents.

It is also noted that the claims may include reference signs/numerals in accordance with PCT Rule 6.2(b). However, the present claims should not be considered to be limited to the exemplary embodiments corresponding to the reference signs/numerals.

What is claimed is:

1. A method for automatic contrast enhancement for contouring, comprising:
    displaying a volumetric image slice to be analyzed;
    receiving a user delineation of a target anatomic structure in the volumetric image slice;
    identifying a region of interest based upon an area being delineated in the volumetric image slice, wherein if the user delineation is not received, the method identifies the entire volumetric image slice as the region of interest;
    analyzing voxel intensity values in the region of interest; and
    determining an appropriate window-level setting based on the voxel intensity values,
    wherein the region of interest is continuously identified, the voxel intensity values of the region of interest analyzed and the appropriate window-level setting determined as the target anatomic structures is delineated.

2. The method of claim 1, further comprising: adjusting a current window-level setting based on the appropriate window-level setting.

3. The method of claim 1, further comprising: storing a series of volumetric images in a memory, wherein the volumetric image slice is one of the series of volumetric images.

4. The method of claim 3, wherein an appropriate window-level setting is automatically determined from one volumetric image slice to another.

5. The method of claim 1, wherein analyzing the voxel intensity values includes forming an intensity histogram.

6. The method of claim 1, further comprising: storing a completely delineated image slice in a memory.

7. The method of claim 1, further comprising: contouring the target anatomic structure based on a delineated series of image slices, the delineated series of image slices including a completely delineated image slice.

8. A system, comprising:
a display displaying a volumetric image slice to be analyzed;
a user interface capable of accepting a user delineation of a target anatomic structure in the volumetric image slice, wherein if the user delineation is not received, the system identifies the entire volumetric image slice as the region of interest; and
a processor identifying a region of interest based on the user delineation and analyzing voxel intensity values of the region of interest to determine an appropriate window-level setting, wherein the region of interest is continuously identified, the voxel intensity values of the region of interest analyzed and the appropriate window-level setting determined as the target anatomic structures is delineated.

9. The system of claim 8, the processor adjusting a current window-level setting based on the appropriate window-level setting.

10. The system of claim 9, further comprising a memory storing a series of volumetric images in a memory, wherein the volumetric image slice is one of the series of volumetric images.

11. The system of claim 9, wherein the memory stores a completely delineated volumetric image slice.

12. The system of claim 10, wherein the processor automatically determines an appropriate window-level setting from one volumetric image slice to another.

13. The system of claim 8, wherein the processor forms an intensity histogram to analyze the voxel intensity values.

14. The system of claim 8, wherein the processor contours the target anatomic structure based on a delineated series of images slices, the delineated series of image slice including a completely delineated image slice.

15. The system of claim 8, wherein the user interface includes a touch sensitive screen.

16. A non-transitory computer-readable storage medium including an executable program stored thereon, wherein the program instructs a processor to perform operations comprising:
displaying a volumetric image slice to be analyzed;
receiving a user delineation of a target anatomic structure in the volumetric image slice;
identifying a region of interest based upon an area being delineated in the volumetric image slice, wherein if the user delineation is not received, the processor identifies the entire volumetric image slice as the region of interest;
analyzing voxel intensity values in the region of interest; and
determining an appropriate window-level setting based on the voxel intensity values,
wherein the region of interest is continuously identified, the voxel intensity values of the region of interest analyzed and the appropriate window-level setting determined as the target anatomic structures is delineated.

* * * * *